United States Patent [19]

Lange et al.

[11] Patent Number: 4,525,340

[45] Date of Patent: Jun. 25, 1985

[54] COMPOSITE BODY FOR LONG-TERM DELIVERY OF EFFECTIVE SUBSTANCES

[75] Inventors: Wolfgang Lange, Obernburg, Fed. Rep. of Germany; G. J. Boer, Muidenberg, Netherlands

[73] Assignee: Akzo NV, Arnhem, Netherlands

[21] Appl. No.: 486,846

[22] Filed: Apr. 20, 1983

[30] Foreign Application Priority Data

Apr. 21, 1982 [DE] Fed. Rep. of Germany ....... 3214667

[51] Int. Cl.³ .......................... A61J 3/00; A61K 9/00
[52] U.S. Cl. ........................................ 424/16; 424/19; 424/21; 424/35; 428/315.5; 604/890; 604/892
[58] Field of Search ...................... 604/890, 891, 892; 428/315.5, 315.7, 315.9; 424/16, 19, 21, 35

[56] References Cited

U.S. PATENT DOCUMENTS

| | | | |
|---|---|---|---|
| 3,985,298 | 10/1976 | Nichols | 428/315.5 |
| 4,164,560 | 8/1979 | Folkman et al. | 424/22 |
| 4,235,236 | 11/1980 | Theeuwes | 604/892 |
| 4,309,996 | 1/1982 | Theeuwes | 604/892 |
| 4,357,312 | 11/1982 | Hsieh et al. | 424/15 |
| 4,391,797 | 7/1983 | Folkman et al. | 424/19 |
| 4,449,983 | 5/1984 | Cortese et al. | 604/892 |
| 4,450,198 | 5/1984 | Michaels | 428/315.5 |

*Primary Examiner*—William J. Van Balen
*Attorney, Agent, or Firm*—Michael J. Striker

[57] ABSTRACT

A composite body for long-term delivery of effective substances has a carrier for effective substances composed of a microporous polymer, and a coating composed of cellulose nitrate. The carrier can be composed of a thermoplastic polymer with a substantially isotropic microporous cellular polymer structure with a plurality of substantially spherical cells of a mean diameter between 0.5 and 100 micrometers. The cells are connected with one another by pores. The composite body serves for long-term delivery of peptides, hormones, neurotransmitters, particularly vasopressin and oxytocin.

13 Claims, No Drawings

COMPOSITE BODY FOR LONG-TERM DELIVERY OF EFFECTIVE SUBSTANCES

BACKGROUND OF THE INVENTION

The present invention relates to a composite body for long-term delivery of effective substances, such as multi-layer membranes, multi-layer hollow fibers, or porous powder provided with a skin or a membrane layer, etc., which deliver over a long period effective material in identical quantities, such as pharmaceutics, hormones, chemicals, etc.

New and improved effective materials are always developed for the pharmaceuticals industry. In contrast, the methods of application of such effective materials have not been changed. The majority of medicaments are always applied orally or, more seldom, under the skin, intramuscularly or intravenously. The dosing of the effective substance for a successive therapy often has the same great importance as the effective substance itself.

For eliminating the disadvantages of the conventional application, it has been proposed to deliver the effective substance from a storage with a certain rate. There are, for example, so-called microcapsules in which the effective material, in general a medicament, is surrounded by a membrane. In this case, it is possible to control the discharge speed of the medicament, for example, by the structure of the membrane, its thickness, selection of the polymer for the membrane, and the like. It has also been proposed to load microporous powder with effective substances, such as fertilizers, insecticides, etc., which deliver in the course of time the effective material to its surroundings.

In all the above described methods, it cannot be in many cases avoided that at least in the initial period an increased delivery of the effective substance takes place, or a so-called "burst" effect. During the course of time, frequently the quantity of delivered effective substance decreases, despite the fact that the storage has not been exhausted.

It is also known to use in such processes composite membranes or porous grains which contain an effective material and are provided with an impregnating substance. The European Pat. No. 5,302 discloses, for example, a process in accordance with which the grains are loaded with an effective material, and a polyurethane skin is formed by chemical reaction to close the pores. Such a method is complicated and difficult. Despite the fact that a whole range of bodies for the long-term delivery of effective materials is known, there is a demand for improved bodies for the long-term delivery.

SUMMARY OF THE INVENTION

Accordingly, it is an object of the present invention to provide a composite body which can be produced in a simple and effective way and forms such a carrier for effective substances which uniformly delivers the effective substance over a long time to the surroundings.

It is also an object of the present invention to provide a composite body which is not easily blocked by the outer surroundings, for example by clogging or formation of a skin which reduces or completely stops the delivery of the effective substance.

It is a further object of the present invention to provide a composite body for long-term delivery of effective substance, the body being not permeable for a plurality of substances located in the outer surroundings and capable of deactivating the effective substances.

In keeping with these objects and with others which will become apparent hereinafter, one feature of the present invention resides, briefly stated, in a composite body for long-term delivery of effective substances, which has a carrier formed by a microporous polymer, and a coating composed of cellulose nitrate.

When the composite body is formed in accordance with the present invention, it attains the above described objects.

The novel features which are considered characteristic for the invention are set forth in particular in the appended claims. The invention itself, however, both as to its construction and its method of operation, together with additional objects and advantages thereof, will be best understood from the following decription of specific embodiments when read in connection with the accompanying drawing.

DESCRIPTION OF THE PREFERRED EMBODIMENTS

A composite body for long-term delivery of effective substances in accordance with the present invention has a carrier for effective substances and composed of a microporous polymer, and a coating composed of cellulose nitrate.

Advantageously, the carrier is composed of a thermoplastic polymer with a substantially isotropic microporous cellular polymer structure which has a plurality of substantially spherical cells with a mean diameter of substantially between 0.5 and 100 microns and a plurality of pores which connect the neighboring cells, wherein the diameter of the pores is smaller than the diameter of the spherical cells, and the ratio between the average cell diameter and the average pore diameter is substantially between 2:1 and 200:1.

Advantageously, the mean diameter of the cells is substantially between 0.5 and 10 microns, and the mean diameter of the pores is substantially between 0.1 and 1 micron. A microporous polymer formed as a hollow fiber is very suitable as the carrier for the composite body. The hollow fiber advantageously has a smooth outer surface provided with a plurality of openings which occupy between 10 and 90% of the outer surface.

The microporous carrier can be used in form of powder. Polypropylene is very suitable as polymer for the composite body. The hollow space of the carrier, which is composed substantially of the volume of the spherical cells and pores, is equal to substantially between 10 and 90%. It is especially advantageous when the hollow space is equal to substantially between 70 and 80%. The composite body in accordance with the invention is suitable particularly for delivery of peptides, hormones, vasopressin and oxytocin.

The manufacture of bodies with a structure in accordance with the present invention is described in the U.S. Pat. No. 4,247,498, and the reference is made here to the disclosure thereof. A plurality of polymers and specific organic liquids mentioned there can be used for manufacture of bodies having different shapes and different microporous structures in accordance with methods disclosed there. As the polymer for the inventive body basically all plastic polymers can be used. Particularly suitable are polyolefins, such as polypropylene and polyethylene; polyamide is also suitable for manufacturing the inventive body.

The formed carrier can be loaded during its manufacture with the effective substance, or it also can be filled with effective substance after its manufacture in accordance with a method disclosed in the above mentioned U.S. Pat. No. 4,247,498.

Hollow fiber membranes which are used as a carrier of the inventive body can be manufactured in accordance with a method disclosed in the U.S. patent application Ser. No. 061,990. The disclosure of the same is incorporated herein by reference. Microporous powder which is also used as the carrier in the present invention is particularly described in the U.S. Pat. Nos. 4,379,860, 4,454,198 and 4,391,920. The disclosures of these references are also incorporated herein within the frame of the present invention.

In accordance with the invention, the carrier is provided with a coating of cellulose nitrate. Cellulose nitrate is an organic ester of cellulose obtained in different esterifying grades. The nitrogen content is also used as a measure for the esterifying grade. The nitrogen content can be, for example, equal to the value of 10.5 or 12.9. Also higher values up to 14.14% N of the theoretical quantity for the trinitrate are possible.

Collodium is particularly suitable for use as cellulose nitrate in accordance with the present invention. Approximate data of cellulose nitrate and collodium can be found in Römpps Chemie-Lexikon, French publication, Stuttgart (7th Edition), on pages 530–531 and 676.

Formation of the coating of cellulose nitrate or collodium on the carrier can be performed in different ways. Thus, it is possible, for example, to spray a solution of collodium onto the carrier, so that after removal of the solving medium a respective skin of collodium is formed.

In many cases, the carrier can be provided with the coating by single or multiple dipping into a collodium solution and providing intermediate drying steps. The thickness of the coating can be controlled by the degree of concentration of the collodium solution and the frequency of dipping. For many applications, the suitable thickness of the coating lies within the value of 10 and 100 micrometers.

The composite body in accordance with the present invention is used for different purposes when it is necessary to provide long-term delivery of effective substances. They can be used for example in agriculture and forestry in powder or granular form, when the inventive bodies are loaded with effective substances such as insecticides, herbicides, or also fertilizers, trace elements, and the like.

An especially advantageous application of the inventive composite bodies is when they are used for pharmaceutically effective substances, hormones, and the like, which must be brought into human or animal bodies. Thus, for example, a hollow fiber which is welded at its one end can be brought as a probe into a human or animal body, the interior of the probe being filled with an effective substance, for example a hormone, and the hormone is slowly and uniformly delivered into the body.

For very long treatment times, it is possible to fill the probe after a certain time from outside. The probe can be connected also to a supply container.

The composite body in accordance with the present invention is especially advantageous for handling of animal or human medications. An advantageous field of application of the inventive body is the handling of hormones, neurotransmitters, particularly vasopressin and oxytocin.

The hollow fiber shaped carrier, for example of polypropylene, or also a thin hose of the same or similar material can be filled with a vasopressin solution, the hollow fiber or the thin hose can be closed at its both ends for example by welding, and coated with collodium layer outside.

Such a hose or a hollow fiber can be easily introduced or implanted completely or partially into the human or animal body. A hollow fiber can be introduced as a hollow needle directly into a predetermined organ, for example into the brain. In this manner it is possible to provide local or organ-specific applications of hormones.

With the aid of the composite body in accordance with the present invention, it is possible to provide in rats a four-week treatment with vasopressin, during which a uniform constant delivery of the effective material takes place, so that the vasopressin produces in favorable manner an antidiuretic action.

An especial advantage of the inventive body is that it is not permeable for many substances which are located in the surroundings. Thus, for example during treatment with hormones certain proteins do not penetrate into the interior of the carrier and do not deactivate the effective substance. It is guaranteed that over a long time the composite body does not loose its effectiveness.

It is possible to control the speed of delivery by the thickness of the carrier and the coating of cellulose nitrate. In many cases it is sufficient when the skin of cellulose nitrate has a thickness in the range of between 10 and 100 micrometers. A further possibility of the application is when a respectively loaded composite body in accordance with the present invention is implanted under the skin, and after a certain treatment time is removed.

Vasopressin and oxytocin, which are advantageously used in accordance with the invention, are hormones of the pituitary gland posterior lobe. Vasopressin controls the kidney activity. It is also active as neurotransmitter. Neurotransmitter serves in a narrow system for transmission of signals. Vasopressin can also improve the memory.

It is especially unexpected that with the composite bodies in accordance with the present invention a continuous uniform delivery of effective substances is guaranteed over long time periods. It is especially possible to eliminate the initially increased delivery of the effective substance which has been recognized in known microcapsules. Thereby the burst action of the effective substance in the beginning of treatment no longer takes place.

The composite body in accordance with the present invention can be used in many fields. Thus it can be utilized in agriculture and forestry for delivery of fertilizers, trace elements, pesticides, odorous substances, sexually attracting substances, and the like.

The manufacture of the inventive composite body is extremely simple and economical.

It will be understood that each of the elements described above, or two or more together, may also find a useful application in other types of objects differing from the types described above.

While the invention has been illustrated and described as embodied in a composite body for long-term delivery of effective substances, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A composite body for long-term delivery of effective substances, comprising a carrier for effective substance and composed of a microporous thermoplastic polymer with pores containing effective substances; and a coating composed of cellulose nitrate in contact with said microporous polymer.

2. A composite body as defined in claim 1, wherein said microporous has a substantially isothropic microporous cellular polymer structure, said thermoplastic polymer having a plurality of substantially spherical cells with mean diameter of substantially between 0.5 and 100 $\mu$m and a plurality of pores which connect neighboring cells with one another, said pores having a diameter which is smaller than the diameter of said cells, and the ratio of an average diameter of said cells to an average diameter of said pores being equal to substantially between 2:1 and 200:1.

3. A composite body as defined in claim 2, wherein said spherical cells of said thermoplastic polymer have a mean diameter of substantially between 0.5 and 10 $\mu$m, said pores of said thermoplastic polymer having a mean diameter of substantially between 0.1 and 1 $\mu$m.

4. A composite body as defined in claim 1, wherein said carrier composed of microporous polymer is formed as a hollow fiber.

5. A composite body as defined in claim 4, wherein said hollow fiber has a smooth outer surface provided with a plurality of openings, said openings occupying between 10 and 90% of said outer surface.

6. A composite body as defined in claim 1, wherein said carrier composed of microporous polymer is formed as a powder carrier.

7. A composite body as defined in claim 1, wherein said carrier is composed of microporous polypropylene.

8. A composite body as defined in claim 1, wherein said carrier composed of microporous polymer has a hollow space occupying substantially between 10 and 90%.

9. A composite body as defined in claim 8, wherein said hollow space of said carrier composed of microporous polymer occupies substantially between 70 and 80%.

10. A composite body for long-term delivery of peptides, comprising a carrier for peptide and composed of microporous thermoplastic polymer; a coating composed of cellulose nitrate in contact with said microporous polymer; and a peptide accommodated in said microporous carrier.

11. A composite body for long-term delivery of hormones, comprising a carrier for hormone and composed of microporous thermoplastic polymer; a coating composed of cellulose nitrate in contact with said microporous polymer; and a hormone accommodated in said microporous carrier.

12. A composite body for long-term delivery of neurotransmitters, comprising a carrier for neurotransmitter and composed of microporous thermoplastic polymer; a coating composed of cellulose nitrate in contact with said microporous polymer; and a neurotransmitter accommodated in said microporous carrier.

13. A composite body for long-term delivery of vasopressin, comprising a carrier for vasopressin and composed of microporous thermoplastic polymer; a coating composed of cellulose nitrate in contact with said microporous polymer; and a vasopressin accommodated in said microporous carrier.

* * * * *